United States Patent
Chandler et al.

(10) Patent No.: US 8,139,221 B2
(45) Date of Patent: *Mar. 20, 2012

(54) APPARATUS FOR MONITORING THE CURE OF A BONE CEMENT MATERIAL

(75) Inventors: Matthew Chandler, Leeds (GB); Philip Royston, Newbury (GB)

(73) Assignee: Depuy International Limited (GB)

( * ) Notice: Subject to any disclaimer, the term of this patent is extended or adjusted under 35 U.S.C. 154(b) by 442 days.

This patent is subject to a terminal disclaimer.

(21) Appl. No.: 11/915,807

(22) PCT Filed: May 30, 2006

(86) PCT No.: PCT/GB2006/001947
§ 371 (c)(1), (2), (4) Date: Jul. 14, 2008

(87) PCT Pub. No.: WO2006/129070
PCT Pub. Date: Dec. 7, 2006

(65) Prior Publication Data
US 2010/0110436 A1    May 6, 2010

(30) Foreign Application Priority Data
May 28, 2005 (GB) .................................. 0510900.4

(51) Int. Cl.
  *G01N 21/59* (2006.01)
  *G01N 23/12* (2006.01)
(52) U.S. Cl. ................... 356/432; 250/432 R
(58) Field of Classification Search .......... 356/432–444; 434/262; 366/8, 65, 139, 319; 250/372, 250/432 R
See application file for complete search history.

(56) References Cited

U.S. PATENT DOCUMENTS

| | | | |
|---|---|---|---|
| 4,854,716 A | 8/1989 | Ziemann | |
| 5,009,102 A | 4/1991 | Afromowitz | |
| 5,145,250 A * | 9/1992 | Planck et al. | 366/8 |
| 5,505,538 A * | 4/1996 | Earle | 366/139 |
| 5,519,211 A | 5/1996 | Bur et al. | |
| 5,598,005 A | 1/1997 | Wang | |
| 6,210,031 B1 * | 4/2001 | Murray | 366/139 |
| 6,683,280 B1 | 1/2004 | Wofford | |
| 2002/0154028 A1 | 10/2002 | Beique | |
| 2004/0210282 A1 | 10/2004 | Flock | |
| 2007/0089518 A1 * | 4/2007 | Ericson et al. | 73/649 |

(Continued)

FOREIGN PATENT DOCUMENTS

DE     4330061 C     9/1994

(Continued)

OTHER PUBLICATIONS

PCT Written Opinion, 6 pages.

(Continued)

*Primary Examiner* — Sang Nguyen

(57) ABSTRACT

Apparatus for monitoring the cure of a bone cement material provided in a container includes a memory device in which data is stored relating to the time taken for the cement material of the type in the container to cure according to the temperature of the material. A data processor is used to calculate the time taken for the cement material to cure, based on data relating to the temperature of the cement material and data in the memory device relating to extent of cure. An output device is provided for data from the data processor relating to the extent of cure of the cement material in the container.

8 Claims, 5 Drawing Sheets

U.S. PATENT DOCUMENTS

2007/0154874 A1* 7/2007 Sherman et al. .............. 434/262
2009/0084978 A1* 4/2009 Chandler et al. .......... 250/432 R

FOREIGN PATENT DOCUMENTS

| DE | 29607832 | | 10/1996 |
|---|---|---|---|
| DE | 10008481 | A | 9/2001 |
| EP | 0329277 | A2 | 8/1989 |
| EP | 0995981 | A | 4/2000 |
| WO | WO 98/04905 | A1 | 2/1998 |
| WO | WO 2004/025283 | A1 | 3/2004 |

OTHER PUBLICATIONS

International Search Report, dated Mar. 5, 2007, 4 pages.
UK Search Report, dated Sep. 1, 2005, 2 pages.

* cited by examiner

APPARATUS FOR MONITORING THE CURE OF A BONE CEMENT MATERIAL

This invention relates to apparatus and a method for monitoring the cure of a bone cement material.

Bone cements that are used to provide fixation between bone tissue and an implanted prosthesis component are commonly provided by first and second materials which, when they react with one another, lead to the formation of a hard cement material. Examples of bone cement materials include those based on acrylate materials which can react by polymerising to form acrylate polymers. A bone cement composition can include acrylate polymer particles which react with monomer in the polymerisation reaction. A bone cement composition can also include other materials such as fillers, for example barium sulphate, zirconium dioxide, glass particles etc. A bone cement can be formed by mixing a liquid acrylate monomer with powders such as acrylate polymer particles and possibly barium sulphate, zirconium dioxide and/or glass particles. The resulting mixture has a paste or dough-like consistency. As is known, the components of the mixture react, involving polymerisation of the acrylate monomer and copolymerisation with the acrylate polymer particles. The viscosity of the cement composition increases during the reaction, resulting in a hard cement.

It is known that surgical results can be optimized by ensuring that the cement is transferred from a mixing vessel to the prepared bone surface (for example in a prepared bone cavity such as the intramedullary cavity in the femur or the humerus in the cases of a hip joint prosthesis or a shoulder joint prosthesis, or on a bone surface as in the case of a femur or a tibia in a knee joint prosthesis) where the prosthesis component is to be implanted when the cement is partially cured. The extent of the cure should exceed a minimum threshold so that the cement is not too fluid, facilitating handling of the cement and minimizing the risk of the cement flowing undesirably after having been placed in contact with the prepared surface of the bone. As discussed below, the time taken to reach this stage in the cure reaction can be referred to as the End of Waiting Time. However, the extent of the cure should not exceed a maximum threshold, in order that subsequent introduction of the prosthesis component is not compromised, and in order that the cement should be able to penetrate the porous surface structure of the bone tissue.

It is also known that surgical results can be optimized by ensuring that the prosthesis component is placed in contact with the bone cement (for example in a prepared bone cavity such as the intramedullary cavity in the femur or the humerus in the cases of a hip joint prosthesis or a shoulder joint prosthesis, or on a bone surface as in the case of a femur or a tibia in a knee joint prosthesis) when the cement is partially cured (with the extent of cure being greater than the extent of cure when the cement is placed on the prepared bone surface). The extent of the cure should exceed a minimum threshold so that the cement is not too fluid, which could mean that the cement would flow to an undesirable degree when the prosthesis component is deployed. However, the extent of the cure should not exceed a maximum threshold, in order that introduction of the prosthesis component is not compromised.

It is common for a surgeon to determine the extent of cure by feel, involving kneading the cement as it cures, and relying on judgement to assess whether the extent of cure of the cement has reached such a level that it is appropriate to transfer the cement to the prepared bone surface, and to such a level that it is appropriate subsequently to introduce the prosthesis component to the cement. Features of the cement which characterize its extent of cure include viscosity (or firmness), tackiness, and smoothness ("grittiness"). Assessment of these features can be affected by environmental conditions. The speed of cure is affected by the temperature of the cement components when they are mixed and on ambient temperature. A factor such as the perceived tackiness can be affected by temperature and humidity.

Relying on subjective techniques to determine the extent of cure has the disadvantage that the determination is not always reliable, and it can be difficult to train new users of the technique. Furthermore, the nature of the cure reaction is such that it can be affected by variations in conditions, especially temperature. Notably, differences between ambient temperature and the temperature of the surgeon's fingers has he kneads a sample of a bone cement can lead to different cure rates between that sample and the remainder of the cement which is to be used in the procedure. Also, variations in temperature and humidity will affect the perception of the tackiness of the cement when this is assessed by an operator by touching the cement with a finger.

It appears that the number of factors which will affect a determination that a cement has reached a particular extent of cure make it difficult to use a physical measurement to make that determination reliably. These factors include ambient temperature and humidity, the selected mixing technique, the temperature of the operator's hands (if manual mixing is being used). The difficulty of relying on physical measurement techniques is compounded by the fact that changes in the properties of the composition during the early stages of cure can take place rapidly for certain compositions.

It is known that the dielectric properties of certain curable bone cement materials change during the curing reaction. This characteristic has been employed in a measuring device which is disclosed in DE-A-10009481 which includes a pair of capacitor electrodes. A bone cement can be placed between the electrodes. The dielectric properties of the bone cement can be measured by applying a potential difference across the electrodes. The measurement of capacitance can provide an indication of the extent of cure of the bone cement.

According to the present invention, it has been found that reliable estimates of the time taken for a cement material to cure can be obtained using stored data relating to the time taken for a cement to cure at various temperatures, in combination with data relating to the temperature of the cement, measured at least at the start of the cure reaction.

Accordingly, in one aspect, the invention provides apparatus for monitoring the cure of a bone cement material, which comprises:

a. a container for the cement material, b. a memory device in which data is stored relating to the time taken for the cement material of the type in the container to cure according to the temperature of the material, c. a data processor for calculating the time taken for the cement material to cure, based on data relating to the temperature of the cement material and data in the memory device relating to extent of cure, and d. an output device for data from the data processor relating to the extent of cure of the cement material in the container.

In another aspect, the invention provides a method of monitoring the cure of a bone cement material, which comprises calculating the time taken for the cement material to cure, based on (a) data relating to the temperature of the cement material, and (b) data from a memory device relating to the rate of cure of the cement material according to the temperature of the material.

The technique of the present invention has the advantage that it can provide a reliable estimation of the time taken for a bone cement material to cure. For example it can provide the basis for estimating the End of Working Time or the subsequent Hardening Time or both of the material. Information about the cure times for the cement can be derived from measurements of temperature, especially a measurement of the temperature at the start of the cure reaction.

Preferably, the apparatus of the invention includes a temperature sensor for providing data relating to the temperature of the cement material. Preferably, the temperature sensor is arranged to measure the temperature of the cement material in the container. This will often involve the sensor being in contact with the cement in the container. For example, the sensor might be provided in the wall of the container for the cement. It might be preferred for the sensor to monitor the temperature of the cement throughout the cure reaction, for example to provide additional information about the extent of cure. In this case, a suitable temperature sensor should be sensitive to changes in temperature in the range which is encountered during the curing reaction, for example between about 20 and about 90° C. A suitable temperature sensor might have an operating range of 0 to 100° C., and an accuracy of ±0.25° C. The sensor can provide data to the data processor relating to the temperature of the cement material at the beginning of the cure reaction. Preferably, the sensor provides data to the data processor relating to the temperature of the cement material at subsequent stages of the cure reaction, especially throughout the cure reaction.

It is a further advantage of the invention that extent of cure measurements can be obtained promptly after first mixing the components of a curable bone cement composition. The invention therefore avoids the difficulties that would arise if extent of cure measurements were to be derived from measurements of viscosity of a cement composition. Furthermore, extent of cure measurements can be obtained by the technique of the present invention without necessarily having to locate a measurement component within the vessel in which the components of a bone cement composition are mixed. This can be contrasted with the measurement of a characteristic such as viscosity.

It will generally be preferred for the extent of cure data that is used in the technique of the invention to relate to the bone cement material that is to be used in a particular procedure. The cure characteristics of bone cement materials can vary widely. When the apparatus of the invention includes data relating to the cure characteristics of more than one bone cement material, the user of the apparatus should identify the material that is being used so that the appropriate set of data is used.

The extent of cure data can be derived from testing procedures which have been performed on bone cement materials. The extent of cure data can be collected under controlled conditions by appropriately experienced operators. For example, when it is necessary to identify stages in the cure reaction using techniques which are empirical or subjective (such as by monitoring the touch and feel of the cement material as it cures), this can be done under controlled conditions by trained technicians who can recognize through experience the characteristics of the cement at those stages of the cure reaction.

The estimate of the cure times of a bone cement material which is derived from the initial temperature and stored extent of cure data, as described above, can additionally make use of other data derived from the cement, including for example measurement of changes in viscosity, temperature and capacitance.

It is particularly preferred that the estimate of the cure times of a bone cement material which is derived from the initial temperature and stored rate of cure data, as described above, can additionally make use of other data derived from measurement of changes in the opacity of the cement to radiation.

Accordingly, the apparatus of the invention can include:
a. a radiation source from which radiation is directed towards cement in the container,
b. a sensor for detecting radiation from the radiation source which has passed through cement in the container, and for generating a signal according to the intensity of the detected radiation,
c. a data processor for monitoring changes in the intensity of radiation that is detected by the sensor due to changes in the opacity of cement in the container to radiation from the source as it cures. The use of opacity measurements has the advantage that the change in the opacity of a bone cement composition as it cures can be significant which can facilitate accurate measurement. Accurate monitoring the extent of cure of a bone cement composition by monitoring changes in opacity can therefore be easier than by monitoring changes in a dielectric property. The relatively greater changes in opacity, compared with changes in dielectric property, can also mean that the accuracy with which the extent of cure is monitored is less dependent on accurate and frequently repeated calibration. These advantages do not appear to be available from measurement of other physical properties of a bone cement material as it cures.

It is an advantage of the use of opacity measurements in an estimation of the extent of cure of a bone cement material that measurements can be obtained promptly after first mixing the components of curable bone cement composition. The invention therefore avoids the difficulties that would arise if extent of cure measurements were to be derived from measurements of viscosity of a cement composition. Furthermore, extent of cure measurements can be obtained by the technique of the present invention without necessarily having to locate a measurement component within the vessel in which the components of a bone cement composition are mixed. This can be contrasted with a technique which might involve measurement of viscosity.

Use of opacity measurements to monitor extent of cure of a bone cement composition has the advantage that the change in the opacity of a bone cement composition as it cures can be significant which can facilitate accurate measurement. Accurate monitoring the extent of cure of a bone cement composition by monitoring changes in opacity can therefore be easier than by monitoring changes in a dielectric property. The relatively greater changes in opacity, compared with changes in dielectric property, can also mean that the accuracy with which the extent of cure is monitored is less dependent on accurate and frequently repeated calibration. These advantages do not appear to be available from measurement of other physical properties of a bone cement material as it cures.

The use of techniques which measure changes in opacity has the further advantage that apparatus can be constructed relatively easily, using relatively low cost components.

The use of techniques which measure changes in opacity has the additional advantage that the extent of cure can be measured using components which are located outside a container for the cement. Accordingly, known techniques can be used for mixing the cement and for delivering it for use (including the use of mixing paddles, syringe and bowl mixing vessels etc), without interference from the components which are used for measuring the extent of cure.

Suitable radiation sources can include diode devices (LEDs). The power supply for the radiation sources can include control components to minimise variations in radiation output due to variations in power that is supplied to the sources. For example, the power supply can include a smoothing component such as a capacitor. The radiation source or the sensor or both can be mounted in an opaque housing to minimise ingress of radiation from other sources (including ambient radiation). For example, the radiation source or the sensor or both can be mounted in one or more opaque sleeves which can be fitted over the relevant part of the container in order to minimise inaccuracies due to ingress of radiation. The sleeve can be provided as a fabric sleeve, especially a resilient fabric. This can have the advantage of being a tight fit around the container. The sleeve can be provided in a solid sleeve, in the form of a block, which can be fitted around at least part of the container so as to enclose it.

Radiation sources which can be used in the apparatus of the invention include infra red sources and ultraviolet sources, as well as sources with intermediate energies. The wavelength of the radiation can be at least about 1 nm. The wavelength of the radiation can suitably be not more than about 105 nm. Preferably, the radiation will be in the visible range (wavelength preferably at least about 400 nm; wavelength preferably not more than about 700 nm). Ultraviolet radiation can be used (wavelength at least about 1 nm; wavelength not more than about 400 nm). Infrared radiation might be used (wavelength at least about 700 nm; wavelength not more than about 105 nm). The wavelength of the radiation from the or each radiation source will be selected according to factors such as the absorption behaviour of the cement as it cures, and the absorption behaviour of the container for the cement.

The sensor for the radiation can comprise one or more light dependent resistors (LDRs). The sensor for the radiation can comprise one or more photodiode. Preferred features for the sensor include high speed, sensitivity, and tolerance to radiation.

Further details of a technique for monitoring extent of cure of a bone cement by measuring changes in the opacity of the cement are disclosed in the International patent application filed with the present application, with the title "Apparatus for monitoring the cure of a bone cement material" and agents' reference SJB/P211327WO. Subject matter disclosed in the specification of that application is incorporated in this the specification of this application by this reference.

The apparatus of the invention can be used to deliver bone cement to a prepared bone surface for use. For example, the apparatus can comprise a delivery tube (for example for use as a nozzle) through which cement can be displaced for delivery to the prepared surface of a patient's bone. A radiation source and associated sensor (when present) can be located relative to the container such that radiation from the radiation source passes through the delivery tube between the source and the sensor. The radiation source or the sensor or both can be located in the wall of a delivery tube, or can be located outside the delivery tube so that the radiation passes through the wall of the delivery tube.

The apparatus can include an output device for displaying information based on data from the data processor relating to changes in the opacity of the cement as it cures. The output device can display the data graphically. The output device can display the absolute values of data. Many types of conventional data output devices will be suitable for use in the apparatus of the invention, including monitors and printers.

The technique of the invention should include calibration steps in which changes in characteristics of a bone cement material (in particular, changes in opacity and changes in temperature) are related to the extent of cure. A characteristic which is important in relation to the extent of cure is the viscosity of the cement; this can often be the characteristic which can affect the effectiveness of the fixation of an implanted prosthesis component in bone tissue which is provided by the cement. The calibration can involve measuring the intensity of the radiation that is detected by the sensor and comparing the variations of intensity with the viscosity of the cement as monitored using viscosity measuring apparatus under known controlled conditions. The viscosity measurements can enable (a) the condition of the cement for transfer from a mixing vessel to the prepared bone surface, (b) the condition of the cement for placing the prosthesis component in contact with the bone cement, and (c) the condition of the cement when it is essentially fully cured, to be identified. The viscosity of a cement material can be monitored during a calibration step in which the cure characteristics of a cement are assessed using appearance and handling characteristics. Relevant stages in the cure of a cement are the "End of Waiting Time", the "End of Working Time", and the "Hardening Time".

End of Waiting Time is the point at which a curing cement has achieved homogeneity characterized by a consistent doughy texture and low adhesion to the finger of a technician who is wearing a clean latex glove. This is significant because it marks the time at which the surgeon is able to manipulate the cement for supply to a body cavity: this is often done by hand, requiring the cement to be adequately mixed, but not sticky. End of Working Time is the point at which a curing cement is no longer workable, characterized by little or no adhesion when a sample of the cement is folded so that two surfaces are in contact and are then pressed together. The cement has reached the End of Working Time when the surfaces can be separated without strands extending between them. This is significant because a prosthesis component must be implanted in a bone cavity while the cement is still workable to ensure that it can flow around the component to achieve secure fixation.

Hardening Time is the point at which a cement has cured sufficiently for it to be able to support a prosthesis component stably within a bone cavity so that the surgeon does not any longer have to support the component to maintain its position and orientation.

The following test routines describe how the End of Waiting Time, the End of Working Time and the Hardening Time are determined:

Determination of End of Waiting Time

1. The cement composition components (generally a powder and a liquid) are mixed according to the manufacturer's instructions.
2. Finger pressure is applied to the surface of the mixed composition using a clean latex glove.
3. The gloved finger is lifted from the cement surface, while monitoring for adhesion between the surface and the gloved finger as shown by cement "fibres".
4. Steps 2 and 3 are repeated, using clean fingers in different areas of the cement surface, until the gloved finger can be lifted from the surface without fibres extending between the surface and the gloved finger.
5. The End of Waiting Time is the length of the period between starting to mix the cement components and the detection of no fibres between the cement surface and the gloved finger.

6. The dough time measurement is repeated with a second sample of the cement, and repeated again until dough time measurements are obtained which differ by less than 5 s, and the End of Waiting Time is then reported as the average of these measured dough times.

Determination of End of Working Time

1. The cement composition components (generally a powder and a liquid) are mixed according to the manufacturer's instructions (and as described above in relation to the determination of End of Waiting Time).
2. Approximately one minute after the mixture has assumed a doughy consistency, a sample of the mixture is removed from the mixing vessel and is flattened between the finger and thumb of a gloved user.
3. The sample is folded and the facing surfaces are pressed together and then pulled apart.
4. Step 3 is repeated until no fibres are seen extending between the pulled apart surfaces. The period between first mixing the components and the time when the facing surfaces can be separated without fibres extending between them is recorded as the End of Working Time.
5. The procedure described in steps 1 to 4 is repeated with a second sample of the cement, and repeated again until end of working time measurements are obtained which differ by less than 5 s, and the End of Working Time is then reported as the average of these measured end of working times.

Determination of Hardening Time

1. The cement composition components (generally a powder and a liquid) are mixed according to the manufacturer's instructions (and as described above in relation to the determination of End of Waiting Time).
2. After the mixture has assumed a doughy consistency, a sample of the mixture is removed from the mixing vessel using a spatula.
3. The sample is formed into a disk by placing it within a PTFE ring which is on the surface of a glass block. The surface of the sample is flattened using a second glass block which is a sliding fit within the PTFE ring. The second glass block is then removed.
4. The extent of cure is monitored by applying a metal probe rod (diameter about 7 mm) to the surface of the cement disk, the probe having a blunt rounded end.
5. A setting time instrument is used to identify when the cement has set. The instrument includes a needle which can be lowered on to the surface of the cement, carrying a load of 5 kgf load.
6. The needle is lowered on to different portions of the surface of the cement until it no longer penetrates the surface.
7. The procedure described in steps 1 to 5 is repeated with a second sample of the cement, and repeated again until setting time measurements are obtained which differ by less than 15 s, and the Hardening Time is then reported as the average of these measured setting times.

The apparatus can include a temperature sensor which monitors the temperature of the cement material at the beginning of and during the cure reaction. The temperature of the cement material can affect the rate of cure significantly. Information about the temperature of the material during the early stages of the cure reaction can help in accurate estimation of the end of working and setting times from changes in measured opacity.

Examples of bone cement compositions and data relating to their cure rates are described below. The cement materials which are referred to in the examples are commercially available from the DePuy CMW division of DePuy International Limited.

In line with the manufacturer's guidelines, features of techniques for handling the described cements include:
1. The cement composition components are stored prior to use at a temperature not exceeding 25° C., without exposure to light.
2. The cement composition components are equilibrated to the ambient temperature conditions prior to mixing.
3. The relative amounts of the cement composition components are as specified by the manufacturer.
4. Mixing is preferably performed in an evacuated container in order to reduce mixing times.
5. The mixing conditions should be selected to minimise entrapment of air, using techniques which are known.
6. Cement can be applied to the patient's bone manually or using a syringe.

A: CMW Cements

|  | Cement | CMW Radiopaque | CMW2 | CMW3 | CMW2000 | Endurance |
|---|---|---|---|---|---|---|
| Bone cement powder | Polymethyl methacrylate (% w/w) | 88.85 | 86.70 | 88.00 | 75.08 | 67.05 |
|  | MM/EM/S copolymer[1] (% w/w) | — | — | — | 14.52 | — |
|  | MM/S copolymer[2] (% w/w) | — | — | — | — | 21.10 |
|  | Butyl peroxide (% w/w) | 2.05 | 2.00 | 2.00 | 2.30 | 1.85 |
|  | Barium sulphate (% w/w) | 9.10 | 11.30 | 10.00 | 8.00 | 10.00 |
| Liquid | Methyl methacrylate (% w/w) | 99.18 | 98.75 | 97.50 | 98.00 | 98.00 |
|  | N,N-dimethyl-p-toluidine (% w/w) | ≦0.82 | ≦1.25 | ≦2.50 | ≦2.00 | ≦2.00 |
|  | Hydroquinone (ppm) | 25 | 25 | 25 | 75 | 75 |

[1] methyl methacrylate/ethyl methacrylate/styrene terpolymer
[2] methyl methacrylate/styrene copolymer Benzoyl peroxide is included as a polymerisation initiator. Hydroquinone is included as a stabilizer to prevent premature polymerisation, for example due to exposure to heat or to light. N,N-dimethyl-p-toluidine is included to promote polymerisation following mixture of the liquid and powder components.

The compositions described above have been found to have mixing, waiting, working and hardening times, determined using the test procedures described above as follows. The times are all measured in seconds from the start of the mixing step.

Manual Application

|  | Mixing temp | CMW1 Radi- opaque | CMW2 | CMW3 | CMW2000 | Endur- ance |
|---|---|---|---|---|---|---|
| End of mixing time | 19° C. | 45 | 35 | 45 | 35 | 30 |
|  | 23° C. | 35 | 30 | 40 | 30 | 25 |
|  | 25° C. | 25 | 25 | 35 | 20 | 25 |

-continued

|  | Mixing temp | CMW1 Radi-opaque | CMW2 | CMW3 | CMW2000 | Endur-ance |
|---|---|---|---|---|---|---|
| End of waiting time | 19° C. | 90 | 70 | 175 | 110 | 240 |
|  | 23° C. | 70 | 50 | 135 | 90 | 165 |
|  | 25° C. | 65 | 40 | 110 | 75 | 120 |
| End of working time | 19° C. | 570 | 320 | 675 | 655 | 830 |
|  | 23° C. | 400 | 230 | 460 | 455 | 580 |
|  | 25° C. | 255 | 150 | 300 | 270 | 385 |
| End of hardening time | 19° C. | 750 | 390 | 765 | 855 | 995 |
|  | 23° C. | 505 | 285 | 540 | 595 | 665 |
|  | 25° C. | 355 | 225 | 395 | 435 | 480 |

Syringe Application

|  | Mixing temp | CMW1 Radi-opaque | CMW3 | CMW2000 | Endur-ance |
|---|---|---|---|---|---|
| End of mixing time | 19° C. | 45 | 45 | 35 | 30 |
|  | 23° C. | 35 | 40 | 30 | 25 |
|  | 25° C. | 25 | 35 | 20 | 25 |
| End of waiting time | 19° C. | 160 | 310 | 260 | 330 |
|  | 23° C. | 110 | 180 | 160 | 220 |
|  | 25° C. | 95 | 135 | 90 | 180 |
| Maximum extrusion time | 19° C. | 520 | 615 | 630 | 770 |
|  | 23° C. | 330 | 435 | 420 | 480 |
|  | 25° C. | 270 | 300 | 280 | 350 |
| End of working time | 19° C. | 635 | 700 | 760 | 820 |
|  | 23° C. | 390 | 485 | 490 | 560 |
|  | 25° C. | 310 | 340 | 315 | 425 |
| End of hardening time | 19° C. | 795 | 770 | 860 | 955 |
|  | 23° C. | 530 | 522 | 575 | 655 |
|  | 25° C. | 390 | 375 | 415 | 495 |

The extent of cure of the cement is suitable for extrusion from the syringe in the period between the end of waiting time and maximum extrusion time.

The same periods apply to bone cements in which the composition is varied by inclusion of an antibiotic such as gentamycin sulphate. This can be included in the bone cement powder component in an amount 4.22% by volume, with proportional adjustments to the amounts of the other components of the powder component, as follows:

|  | Cement | CMW1 Gentamycin | CMW2 Gentamycin | CMW3 Gentamycin | CMW2000 Gentamycin | Endurance Gentamycin |
|---|---|---|---|---|---|---|
| Bone cement powder | Gentamycin sulphate (% w/w) | 4.22 | 4.22 | 4.22 | 4.22 | 4.22 |
|  | Polymethyl methacrylate (% w/w) | 84.73 | 82.78 | 83.88 | 71.54 | 65.28 |
|  | MM/EM/S copolymer[1] (% w/w) | — | — | 13.94 | — | — |
|  | MM/S copolymer[2] (% w/w) | — | — | — | — | 18.65 |
|  | Butyl peroxide (% w/w) | 1.95 | 2.00 | 1.90 | 2.30 | 1.85 |
|  | Barium sulphate (% w/w) | 9.10 | 11.00 | 10.00 | 8.00 | 10.00 |
| Liquid | Methyl methacrylate (% w/w) | 99.18 | 99.18 | 97.50 | 98.00 | 98.00 |
|  | N,N-diethyl-p-toluidine (% w/w) | ≦0.82 | ≦0.82 | ≦2.50 | ≦2.00 | ≦2.00 |
|  | Hydroquinone (ppm) | 25 | 25 | 25 | 75 | 75 |

B: CMW SmartSet HV Cements

|  | Cement | SmartSet HV | SmartSet GHV |
|---|---|---|---|
| Bone cement powder | Gentamycin sulphate (% w/w) | — | 4.22 |
|  | Polymethyl methacrylate (% w/w) | 84.00 | 80.46 |
|  | Butyl peroxide (% w/w) | 1.00 | 0.96 |
|  | Zirconium dioxide (% w/w) | 15.00 | 14.37 |

|  | Cement | SmartSet HV | SmartSet GHV |
|---|---|---|---|
| Liquid | Methyl methacrylate (% w/w) | 97.50 | 97.50 |
|  | N,N-dimethyl-p-toluidine (% w/w) | ≦2.50 | ≦2.50 |
|  | Hydroquinone (ppm) | 75 | 75 |

The compositions described above have been found to have mixing, waiting, working and hardening times, determined using the test procedures described above as follows. The times are all measured from the start of the mixing step.

|  | Initial mixing temp | Manual application | | Syringe application | |
|---|---|---|---|---|---|
|  |  | SmartSet HV | SmartSet GHV | SmartSet HV | SmartSet GHV |
| End of mixing time | 19° C. | 30 | 30 | 30 | 30 |
|  | 23° C. | 30 | 30 | 30 | 30 |
|  | 25° C. | 25 | 25 | 25 | 25 |
| End of waiting time | 19° C. | 65 | 65 | 90 | 80 |
|  | 23° C. | 50 | 50 | 90 | 80 |
|  | 25° C. | 40 | 35 | 85 | 80 |
| Maximum extrusion time | 19° C. | — | — | 580 | 660 |
|  | 23° C. | — | — | 415 | 460 |
|  | 25° C. | — | — | 275 | 350 |
| End of working time | 19° C. | 680 | 705 | 650 | 705 |
|  | 23° C. | 480 | 500 | 460 | 500 |
|  | 25° C. | 340 | 390 | 310 | 390 |
| End of hardening time | 19° C. | 815 | 870 | 810 | 870 |
|  | 23° C. | 605 | 660 | 600 | 660 |
|  | 25° C. | 465 | 510 | 450 | 510 |

Data relating to the mixing, waiting, working, maximum extrusion and hardening times of different bone cement compositions over a range of temperatures can be compiled from data of the kind that is set out above for particular bone cement compositions that are currently sold by DePuy International Limited. As can be seen, these times are dependent on the temperature of the cement. It is preferred that the data relating to the mixing, waiting, working and hardening times reflects the temperature dependence of the times. It is possible with suitable data processing apparatus to interpolate and to extrapolate to provide an indication of the mixing, waiting, working, maximum extrusion and hardening times of bone cement compositions at temperatures which are less than, between, or greater than those at which specific measurements have been made.

According to the present invention, apparatus for monitoring the cure of a bone cement material includes a data processor and an output device. In use, the apparatus is provided with data as to (a) the nature of the cement material, and preferably (b) the temperature of the cement material. When the apparatus is intended for use with a single cement material, information as to the nature of the cement material can be provided prior to use, for example when the apparatus is manufactured. With this information, and especially with information as to the temperature of the cement material, the apparatus is able through the output device to provide information as to the end of the waiting, maximum extrusion, working and hardening times for the cement under consideration.

The apparatus of the present invention can be used stand alone to provide an indication as to the extent of cure of a bone cement material. It can incorporate features of apparatus which monitors changes in the opacity of the cement as it cures, for example as disclosed in the UK patent application filed with the present application, with the title "Apparatus for monitoring the cure of a bone cement material" and agents' reference SJB/P211038. For example, the apparatus of the invention can provide estimates of the extent of cure based both on time and temperature data and on opacity measurements. It will be expected in most circumstances that the two estimates should produce closely similar indications of the extent of cure. Different estimates will provide an indication to the user of an anomaly in at least one of the estimation techniques.

Embodiments of the invention will now be described by way of example with reference to the accompanying drawings, in which.

Figure 1A:
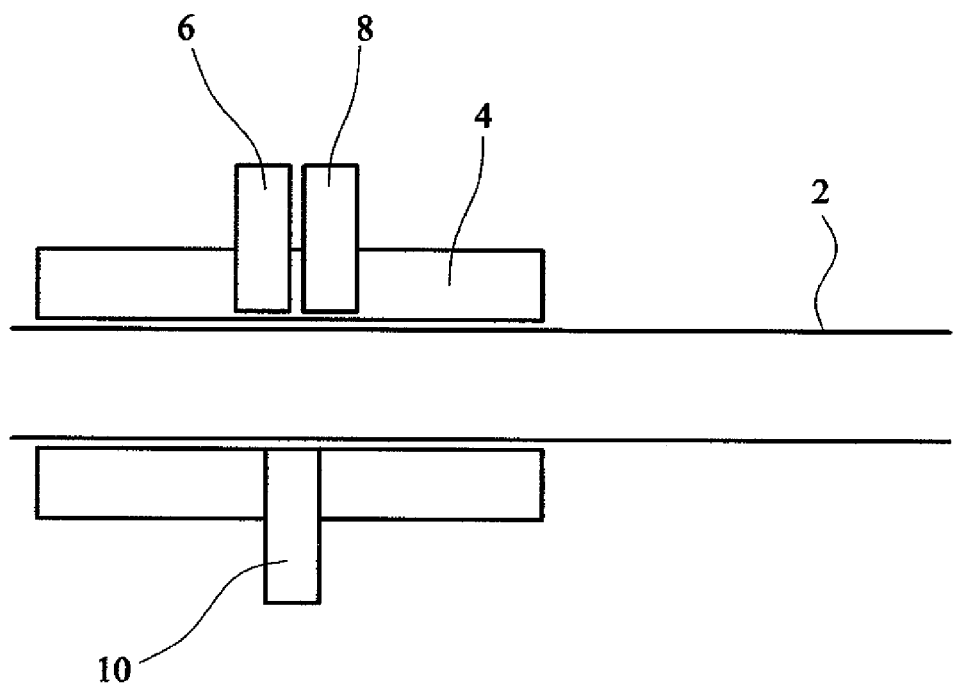
FIGS. 1a and 1b are schematic drawings of radiation source/sensor arrangements which can be used in the technique of the present invention.

Referring to the drawings, FIG. 1a shows a tubular vessel 2 which is part of apparatus for monitoring the cure of a bone cement. The vessel can be a delivery tube extending from a mixing vessel such as a syringe. The tubular vessel is made from a polymeric material such as a polypropylene.

The tubular vessel 2 has an opaque sleeve 4 fitted around it. Two light emitting diodes (LEDs) 6, 8 are mounted in the sleeve so that radiation which is emitted from the diodes is directed into the wall of the tubular vessel. A sensor 10 for detecting radiation from the radiation source which has passed through the tubular vessel, and for generating a signal according to the intensity of the detected radiation, is mounted in the sleeve. The sleeve 4 is opaque to radiation having the wavelength that is emitted from the diodes so that any signal that is generated by the sensor in response to radiation received from the LEDs is not made inaccurate by radiation which is derived from external sources.

The LEDs 6, 8 can emit radiation with different wavelengths. For example, one of the LEDs 6 can emit radiation with a wavelength of 400 nm and the other of the LEDs 8 can emit radiation with a wavelength of 810 nm. The LEDs 6, 8 can emit radiation with the same wavelength, for example 400 nm or 810 nm, or another wavelength.

Figure 1B:
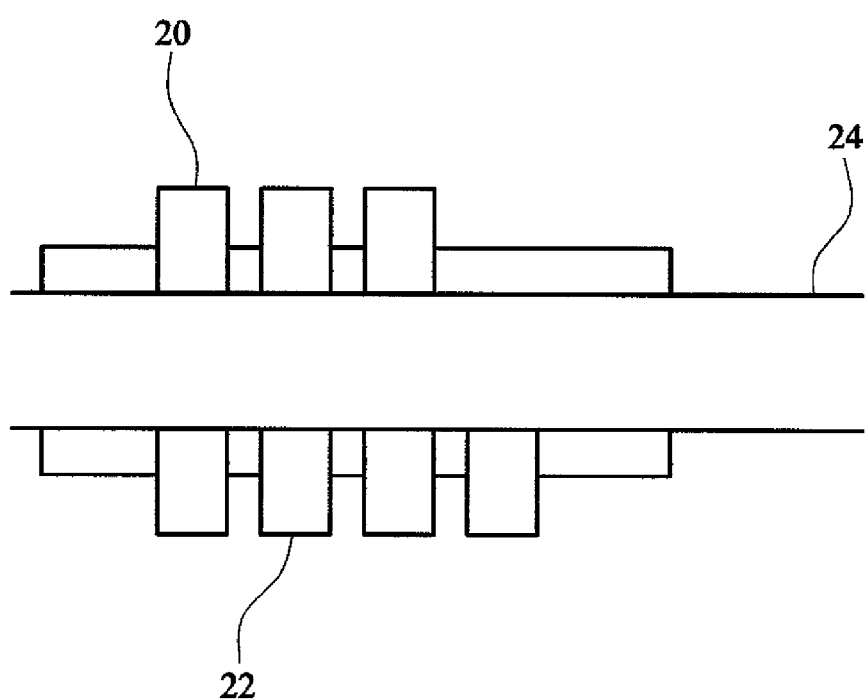

The LEDs 6, 8 and the sensor 10 are arranged so that the sensor is not directly opposite to either of the LEDs. Instead, the sensor is located between the positions which are directly opposite to the LEDs. Especially when the apparatus includes two or more sensors, it can be preferred for each sensor to be offset relative to the midpoint between two radiation sources. This has the advantage that inaccuracies due to internal reflections can be minimized. This is shown in FIG. 1b in which monitoring apparatus comprises three radiation sources 20 and three sensors 22. The apparatus might include an opaque sleeve but this is not shown. The distance "d" between adjacent radiation sources is the same as the distance between adjacent sensors. The sensors are displaced along the tubular vessel 24 relative to the radiation sources by a distance which is about 0.6 d.

Figure 2A:
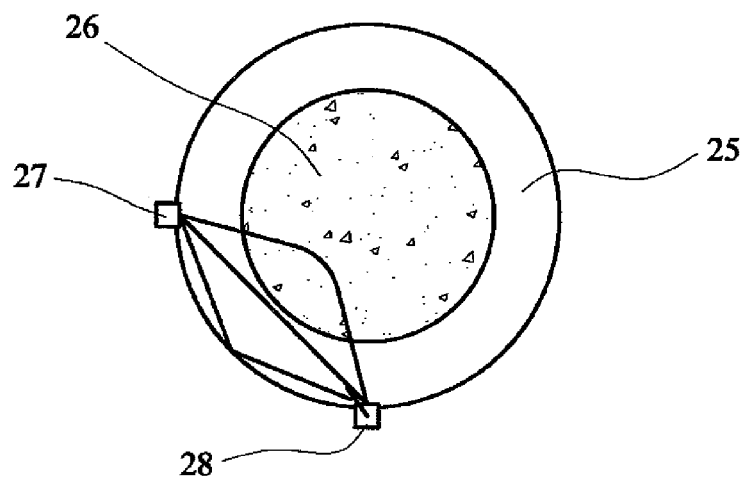
FIGS. 2a and 2b are cross-sections through a cement delivery tube showing the relative positions of a radiation source and a sensor.

FIG. 2a is a cross-section through a cement delivery tube such as a tube which is used to delivery mixed cement from a syringe. The tube has a wall 25 which defines a central passageway 26 through which cement can be delivered from a mixing vessel to a prepared bone surface.

A radiation source 27 and a sensor 28 are mounted on the external surface of the tube wall, for example by means of a tight fitting opaque sleeve as described above (but not shown). Each of them is directed towards the centre of the tube so that radiation that is emitted from the source is directed radially. The source is capable of receiving radiation from a range of directions, but is similarly directed towards the centre of the tube.

In FIG. 2a, the radiation source 27 and the sensor 28 are arranged adjacent to on another so that the angle between the axes of the source and the sensor is about 90°. Radiation that is received directly by the sensor from the source is transmitted through the material of the wall 25. In addition, some radiation can be received indirectly after transmission through the material of the wall, with some scattering. Radiation that is received by the sensor from the source after passing through cement does so as a result of scattering by the cement.

Figure 2B:
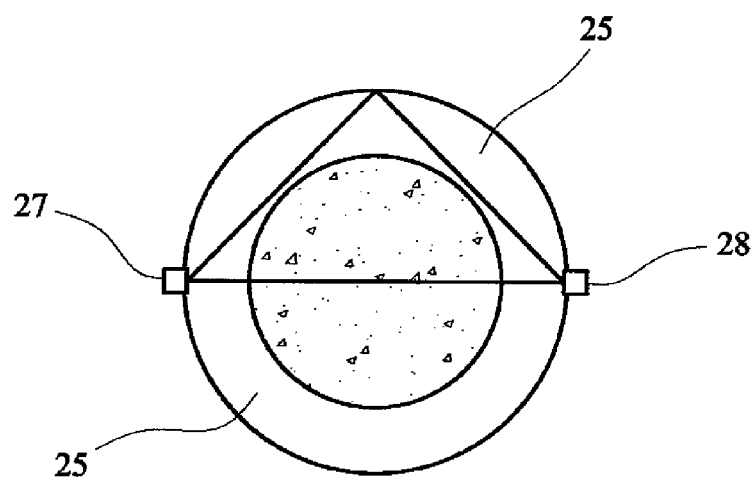

In FIG. 2b, the axis of the radiation source 27 and the sensor 28 are coincident so that radiation that is received by the sensor after passing through the cement passes straight through the tube from the source on one side of the tube to the sensor on the opposite side.

The relative merits of the configurations shown in FIGS. 2a and 2b will depend on the transmission characteristics towards the selected radiation of the cement and the material of the tube wall 25.

Figure 3:
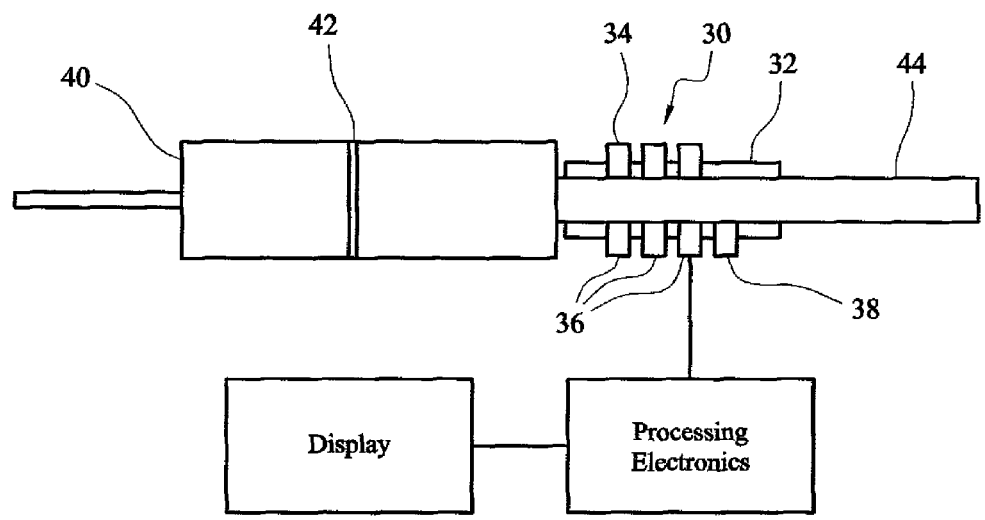
FIG. 3 is a schematic drawing of apparatus according to the present invention.

FIG. 3 shows apparatus according to the invention which includes a radiation source/sensor arrangement 30 of the general kind described above in relation to FIG. 1. The apparatus includes an opaque sleeve 32 which has three LEDs 34 and three sensors 36 mounted in it. The sleeve also has a temperature sensor 38 mounted in it.

The apparatus includes a syringe which comprises a syringe barrel 40 having a piston 42 which can slide therein. The syringe barrel 40 can be used to mix components of a bone cement material for delivery to a patient's bone. Syringe based mixing vessels for bone cement materials are well known. The syringe includes a delivery tube 44. Movement of the piston through the syringe barrel 40 results in displacement of mixed bone cement through the delivery tube 44.

Figure 4:
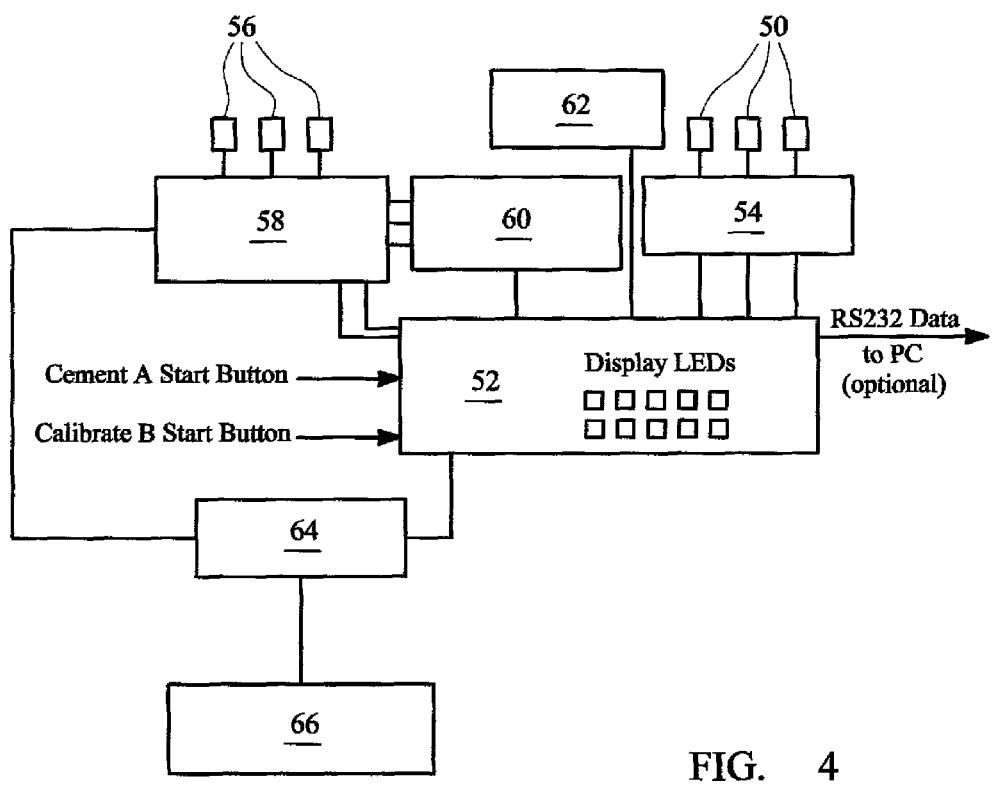
FIG. 4 is a block diagram showing components of the control components for the apparatus of the invention.

FIG. 4 shows details of the control components for the apparatus of the invention. The apparatus includes three LEDs 50 which are controlled by a data processor 52 through constant voltage power drivers 54. The apparatus includes three photodiode sensors 56. Data from the photodiode sensors are passed through a signal conditioning unit 58 and an analog-to-digital converter unit 60 to the processor 52. The apparatus includes a temperature sensor 62. Data from the temperature sensor are passed to the processor 52. The apparatus includes a power supply 64, which can include a rechargeable battery 66.

The processor can include a connector for a data output cable, for example to supply data to an external display or to a computer for further manipulation or storage or both. The processor can include a display, for example in the form of a plurality of display light emitting diodes.

Figure 5:
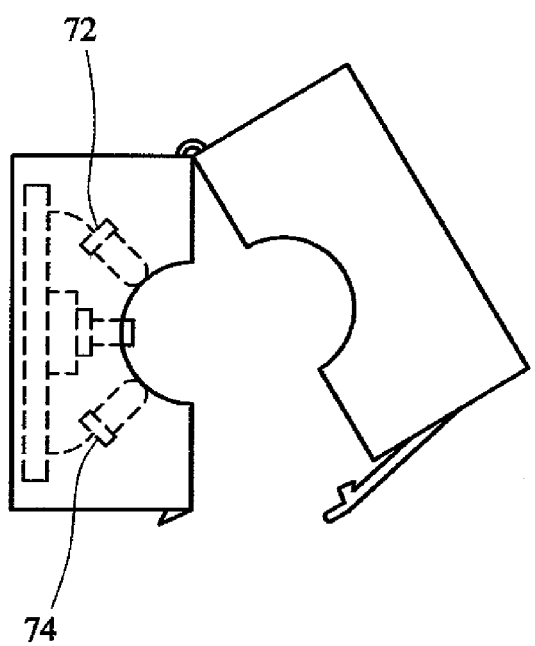
FIG. 5 is a side view, with hidden details shown in dotted outline, of a sensor head which can be fitted on to a cement delivery tube.

FIG. 5 shows a sensor head 70 which can be fitted on to a delivery tube. The sensor head can be formed in two parts which, when fitted against one another, define a tubular bore extending through the head which is a tight fit on to a delivery tube. The parts of the sensor head can be connected to one another by a hinge, allowing the sensor head to be opened to fit on to or to be removed from a delivery tube. The sensor head can include a latch for closing the parts of the head once fitted on to a delivery tube.

The sensor head can have a radiation source 72 and a sensor 74 fitted within it. This has the advantage that the relative positions of the source and the sensor are fixed, which can help to optimize the accuracy with which opacity measurements can be made.

The sensor head can be made wholly or in part from a material which is opaque, at least to the radiation which is emitted from the source, so that the sensor head can provide an opaque sleeve to prevent ingress of radiation from other sources (including ambient radiation). When the bulk material of the sensor head is not opaque, it can be coated, internally or externally, with a material which is opaque. Suitable materials for the bulk of the sensor head include certain polymers, preferably which can be processed by moulding. Examples include polyolefins, polyesters, polycarbonates etc.

Figure 6:
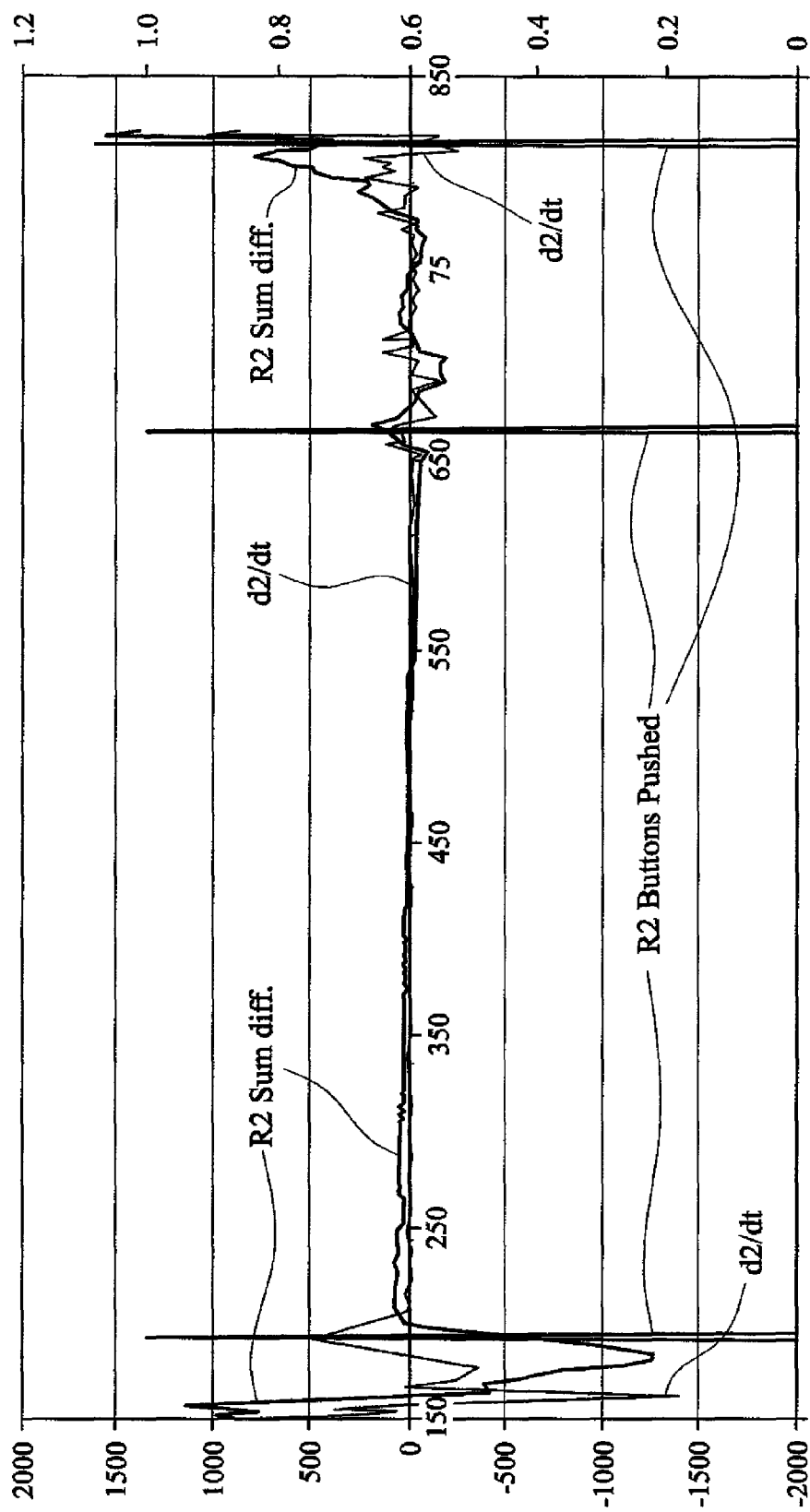
FIGS. 6 and 7 are graphs showing how the optical response varies with time during exposure of two different cement compositions to radiation.
Figure 7:
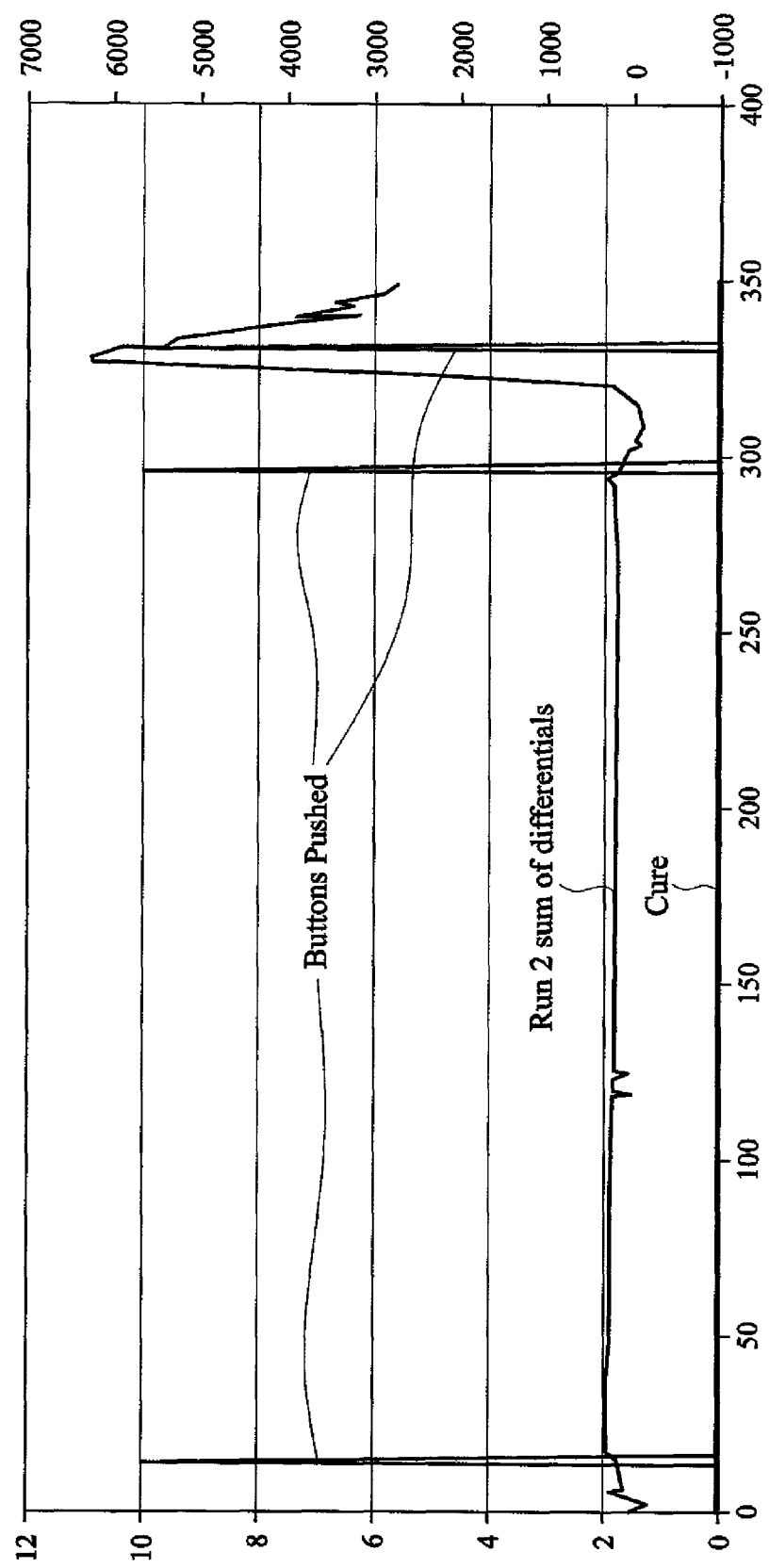

FIGS. 6 and 7 show how opacity changes with time. The data relate to the bone cement materials that are available from the DePuy CMW division of DePuy International Limited under the trade marks SmartSet HV and Endurance, respectively. In FIG. 6, the grey line with reference to the right hand axis represents the variation with time of the sum of the differentials of intensity with respect to time of the signals that are measured at separated wavelengths (such as 400 and 810 nm) using apparatus of the kind described above. This data is generated as follows:
1. The intensity of the detected radiation at each of two wavelengths is sampled every second.
2. The intensity measurement obtained at each of the wavelengths is subtracted from the previous intensity measurement to provide the differential value.
3. The differential value is averaged over 15 seconds, using a rolling average of 15 measured values.
4. The average differential values obtained at the two wavelengths are summed together to provide the sum of differentials data.

The right hand axis relates to these data points. The white line represents the rate of change of the sum of differentials data (the first derivative of the data represented by the grey line) and the left hand scale relates to these data points.

The graph in FIG. 6 has three spikes superimposed on the grey and white lines which correspond to the End of Waiting Time (when the cement is ready to be transferred from a mixing vessel to the prepared bone surface), End of Working Time (when the cement is cured to such an extent that implantation of the prosthesis must have been completed) and Hardening Time of the cement. These are determined with reference to an expert human tester, by manual manipulation of the cement materials and monitoring the characteristics of the cement as it cures, as discussed above. As can be seen, the black line spikes correspond to discontinuities in the grey and white lines, corresponding to the End of Waiting Time, the End of Working Time, and the Hardening Time of the cement.

In FIG. 7, the pale grey line represents the variation with time of the sum of the differentials of intensity with respect to time of the signals that are measured at separated wavelengths (such as 400 and 810 nm) using apparatus of the kind described above. The right hand scale relates to these data points. The graph has three spikes superimposed on the grey line which correspond to the End of Waiting Time (when the cement is ready to be transferred from a mixing vessel to the prepared bone surface), End of Working Time (when the cement is cured to such an extent that implantation of the prosthesis must have been completed) and Hardening Time of the cement. These are determined with reference to an expert human tester, by manual manipulation of the cement materials and monitoring the characteristics of the cement as it cures, as discussed above. As can be seen, the black line spikes correspond to discontinuities in the grey and white lines, corresponding to the End of Waiting Time, the End of Working Time, and the Hardening Time of the cement.

The invention claimed is:

1. An apparatus for monitoring the cure of a bone cement material, comprising:
   a container for the cement material;
   a sensor for measuring the temperature of the cement material in the container while the cement material cures, wherein at least a portion of the sensor is located within the container;
   a memory device in which data is stored relating to the time taken for the cement material of the type in the container to cure according to the temperature of the material;
   a data processor for calculating the time taken for the cement material to cure, based on data relating to the temperature of the cement material and data in the memory device relating to extent of cure; and
   an output device for displaying data from the data processor relating to the extent of cure of the cement material in the container.

2. The apparatus of claim 1, comprising:
   a radiation source from which radiation is directed towards cement in the container; and
   a sensor configured to detect radiation from the radiation source which has passed through the cement in the container, and to generate a signal according to the intensity of the detected radiation.

3. The apparatus of claim 2, wherein the data processor is configured to monitor changes in the intensity of the radiation that is detected by the sensor due to changes in the opacity of cement in the container to radiation from the source as it cures.

4. The apparatus of claim 2, wherein the container includes a delivery tube, and wherein the radiation source and the sensor are located relative to the container such that radiation from the radiation source passes through the delivery tube between the source and the sensor.

5. The apparatus of claim 1, wherein the data processor determines the rate of change of the intensity of radiation that is detected by the sensor due to changes in the opacity of cement in the container to radiation from the source as it cures.

6. The apparatus of claim 1, wherein the sensor is located such that at least a part of the sensor contacts the cement when the cement is being mixed within the container.

7. A method of monitoring the cure of a bone cement material, comprising the steps of:
   measuring the temperature of cement contained within a container while the cement cures; and
   calculating the time taken for the cement material to cure, based on (a) data relating to the temperature of the cement material obtained during curing of the cement material, and (b) data from a memory device relating to the extent of cure of the cement material according to the temperature of the material, wherein the calculating step is performed by a data processor.

8. The method of claim 7, further comprising the steps of:
   exposing the cement to radiation from a radiation source;
   determining the intensity of radiation which has passed through the cement; and
   monitoring changes in the intensity of radiation that is detected by the sensor due to changes in the opacity of cement in the container to radiation from the source as it cures.

* * * * *